United States Patent
Isaacson

(10) Patent No.: US 9,498,158 B2
(45) Date of Patent: Nov. 22, 2016

(54) OPTICAL SENSOR PATH SELECTION

(71) Applicant: Nonin Medical, Inc., Plymouth, MN (US)

(72) Inventor: Philip O. Isaacson, Chanhassen, MN (US)

(73) Assignee: Nonin Medical, Inc., Plymouth, MN (US)

( * ) Notice: Subject to any disclaimer, the term of this patent is extended or adjusted under 35 U.S.C. 154(b) by 0 days.

(21) Appl. No.: 14/244,256

(22) Filed: Apr. 3, 2014

(65) Prior Publication Data

US 2014/0221798 A1    Aug. 7, 2014

Related U.S. Application Data

(62) Division of application No. 12/618,120, filed on Nov. 13, 2009, now Pat. No. 8,725,226.

(60) Provisional application No. 61/114,528, filed on Nov. 14, 2008.

(51) Int. Cl.
    *A61B 5/1455*    (2006.01)
    *A61B 5/00*      (2006.01)

(52) U.S. Cl.
    CPC ....... *A61B 5/14552* (2013.01); *A61B 5/14553* (2013.01); *A61B 5/6814* (2013.01); *A61B 2562/0233* (2013.01); *A61B 2562/0242* (2013.01); *A61B 2562/043* (2013.01)

(58) Field of Classification Search
    CPC ............ A61B 5/1455; A61B 5/14551; A61B 5/14552; A61B 5/6814
    See application file for complete search history.

(56) References Cited

U.S. PATENT DOCUMENTS

| | | |
|---|---|---|
| 2,706,927 A | 4/1955 | Wood |
| 2,790,438 A | 4/1957 | Taplin et al. |
| 3,412,729 A | 11/1968 | Smith, Jr. |
| 3,068,742 A | 8/1969 | Hicks, Jr. et al. |
| 3,461,856 A | 8/1969 | Polyani |
| 3,638,640 A | 2/1972 | Shaw |
| 3,704,706 A | 12/1972 | Herczfeld et al. |
| 3,709,612 A | 1/1973 | Clemens |
| 3,866,599 A | 2/1975 | Johnson |
| 3,998,550 A | 12/1976 | Konishi et al. |

(Continued)

FOREIGN PATENT DOCUMENTS

| | | |
|---|---|---|
| JP | 01146524 A | 6/1989 |
| JP | 05212016 A | 8/1993 |

(Continued)

OTHER PUBLICATIONS

"U.S. Appl. No. 11/078,399, Examiner Interview Summary mailed Jun. 10, 2010", 3 pgs.

(Continued)

*Primary Examiner* — Eric Winakur
(74) *Attorney, Agent, or Firm* — Schwegman Lundberg & Woessner, P.A.

(57) ABSTRACT

A device includes a sensor for measuring a parameter for tissue. The sensor includes a plurality of optical elements including a plurality of detectors and at least one emitter. Separation distances between the various optical elements are selected based on a depth corresponding to a region of interest in the tissue and based on a depth corresponding to an exclusion region in the tissue.

11 Claims, 4 Drawing Sheets

(56) References Cited

U.S. PATENT DOCUMENTS

| | | |
|---|---|---|
| 4,014,321 A | 3/1977 | March |
| 4,029,085 A | 6/1977 | DeWitt et al. |
| 4,086,915 A | 5/1978 | Kofsky et al. |
| 4,119,406 A | 10/1978 | Ciemens |
| 4,129,125 A | 12/1978 | Lester et al. |
| 4,167,331 A | 9/1979 | Nielsen |
| 4,222,389 A | 9/1980 | Rubens |
| 4,223,680 A | 9/1980 | Jobsis |
| 4,224,948 A | 9/1980 | Cramer et al. |
| 4,259,963 A | 4/1981 | Huch |
| 4,266,554 A | 5/1981 | Hamaguri |
| 4,281,645 A | 8/1981 | Jobsis |
| 4,321,930 A | 3/1982 | Jobsis et al. |
| 4,380,240 A | 4/1983 | Jobsis et al. |
| 4,416,285 A | 11/1983 | Shaw et al. |
| 4,447,884 A | 5/1984 | Wade |
| 4,452,250 A | 6/1984 | Chance et al. |
| 4,469,107 A | 9/1984 | Asmar et al. |
| 4,510,938 A | 4/1985 | Jobsis et al. |
| 4,576,173 A | 3/1986 | Parker et al. |
| 4,648,892 A | 3/1987 | Kittrell et al. |
| 4,655,225 A | 4/1987 | Dahne et al. |
| 4,700,708 A | 10/1987 | New, Jr. et al. |
| 4,714,341 A | 12/1987 | Hamaguri et al. |
| 4,738,267 A | 4/1988 | Lazorthes et al. |
| 4,773,422 A | 9/1988 | Isaacson et al. |
| 4,774,679 A | 9/1988 | Carlin |
| 4,800,495 A | 1/1989 | Smith |
| 4,800,885 A | 1/1989 | Johnson |
| 4,805,623 A | 2/1989 | Jobsis |
| 4,824,242 A | 4/1989 | Frick et al. |
| 4,836,207 A | 6/1989 | Bursell et al. |
| 4,840,485 A | 6/1989 | Gratton |
| 4,846,183 A | 7/1989 | Martin |
| 4,869,254 A | 9/1989 | Stone et al. |
| 4,880,304 A | 11/1989 | Jaeb et al. |
| 4,908,762 A | 3/1990 | Suzuki et al. |
| 4,926,867 A | 5/1990 | Kanda et al. |
| 4,942,877 A | 7/1990 | Sakai et al. |
| 4,972,331 A | 11/1990 | Chance |
| 5,032,024 A | 7/1991 | Cope |
| 5,035,243 A | 7/1991 | Muz |
| 5,057,695 A | 10/1991 | Hirao et al. |
| 5,058,588 A | 10/1991 | Kaestle |
| 5,062,431 A | 11/1991 | Potter |
| 5,074,306 A | 12/1991 | Green |
| 5,088,493 A | 2/1992 | Giannini et al. |
| 5,090,415 A | 2/1992 | Yamashita et al. |
| 5,119,815 A | 6/1992 | Chance |
| 5,137,355 A | 8/1992 | Barbour et al. |
| 5,139,025 A | 8/1992 | Lewis et al. |
| 5,140,989 A | 8/1992 | Lewis et al. |
| 5,198,977 A | 3/1993 | Salb |
| 5,213,105 A | 5/1993 | Gratton et al. |
| 5,217,013 A | 6/1993 | Lewis et al. |
| 5,218,962 A | 6/1993 | Mannheimer et al. |
| 5,222,495 A | 6/1993 | Clarke et al. |
| 5,253,646 A | 10/1993 | Delpy et al. |
| 5,261,410 A | 11/1993 | Alfano et al. |
| 5,266,554 A | 11/1993 | Suchy et al. |
| 5,277,181 A | 1/1994 | Mendelson et al. |
| 5,285,783 A | 2/1994 | Secker |
| 5,318,023 A | 6/1994 | Vari et al. |
| 5,349,961 A | 9/1994 | Stoddart et al. |
| 5,385,143 A | 1/1995 | Aoyagi |
| 5,431,170 A | 7/1995 | Mathews |
| 5,465,714 A | 11/1995 | Scheuing |
| 5,477,853 A | 12/1995 | Farkas |
| 5,482,031 A | 1/1996 | Lambert |
| 5,482,034 A | 1/1996 | Lewis |
| 5,490,523 A | 2/1996 | Isaacson et al. |
| 5,497,769 A | 3/1996 | Gratton et al. |
| 5,524,617 A | 6/1996 | Mannheimer |
| 5,529,064 A | 6/1996 | Rall |
| 5,551,422 A | 9/1996 | Simonsen et al. |
| 5,551,423 A | 9/1996 | Sugiura |
| 5,584,269 A | 12/1996 | MacKenzie |
| 5,697,367 A | 12/1997 | Lewis et al. |
| 5,720,284 A | 2/1998 | Aoyagi et al. |
| 5,772,589 A | 6/1998 | Bernreuter |
| 5,779,631 A | 7/1998 | Chance |
| 5,792,052 A | 8/1998 | Isaacson |
| 5,795,292 A | 8/1998 | Lewis et al. |
| 5,800,349 A | 9/1998 | Isaacson et al. |
| 5,873,821 A | 2/1999 | Chance et al. |
| 5,879,294 A | 3/1999 | Anderson et al. |
| 5,902,235 A | 5/1999 | Lewis et al. |
| 5,922,607 A | 7/1999 | Bernreuter |
| 6,226,540 B1 | 5/2001 | Bernreuter |
| 6,285,895 B1 | 9/2001 | Ristolainen et al. |
| 6,526,300 B1 | 2/2003 | Kiani et al. |
| 6,549,795 B1 | 4/2003 | Chance |
| 6,597,931 B1 | 7/2003 | Cheng et al. |
| 6,615,061 B1 * | 9/2003 | Khalil et al. .................. 600/310 |
| 6,615,065 B1 | 9/2003 | Barrett et al. |
| 6,985,763 B2 | 1/2006 | Boas et al. |
| 7,047,054 B2 | 5/2006 | Benni |
| 7,072,701 B2 | 7/2006 | Chen et al. |
| 7,865,223 B1 | 1/2011 | Bernreuter |
| 8,055,321 B2 | 11/2011 | Bernreuter |
| 8,725,226 B2 | 5/2014 | Isaacson |
| 8,923,942 B2 | 12/2014 | Bernreuter |
| 9,364,176 B2 | 6/2016 | Bernreuter |
| 2002/0058865 A1 | 5/2002 | Cheng |
| 2002/0082488 A1 | 6/2002 | Al-Ali et al. |
| 2002/0161290 A1 | 10/2002 | Chance |
| 2002/0198443 A1 | 12/2002 | Ting |
| 2003/0181798 A1 | 9/2003 | Al-Ali |
| 2004/0024297 A1 | 2/2004 | Chen et al. |
| 2005/0075549 A1 | 4/2005 | Kondoh |
| 2005/0228291 A1 | 10/2005 | Chance |
| 2006/0189862 A1 | 8/2006 | Casciani et al. |
| 2007/0055119 A1 | 3/2007 | Lash et al. |
| 2008/0015424 A1 | 1/2008 | Bernreuter |
| 2008/0058638 A1 | 3/2008 | Zhu et al. |
| 2008/0208011 A1 | 8/2008 | Shuler |
| 2009/0247853 A1 | 10/2009 | Debreczeny |
| 2009/0281403 A1 | 11/2009 | Benni |
| 2010/0094134 A1 | 4/2010 | Zhu et al. |
| 2010/0130840 A1 | 5/2010 | Isaacson |
| 2011/0060200 A1 | 3/2011 | Bernreuter |
| 2012/0184830 A1 | 7/2012 | Balberg et al. |
| 2012/0190946 A1 | 7/2012 | Bernreuter |
| 2014/0249390 A1 | 9/2014 | Bernreuter et al. |

FOREIGN PATENT DOCUMENTS

| | | |
|---|---|---|
| JP | 630915 A | 2/1994 |
| JP | 630916 A | 2/1994 |
| JP | 8271600 A | 10/1996 |
| JP | 10507118 A | 7/1998 |
| JP | 11244268 A | 9/1999 |
| JP | 2002303576 A | 10/2002 |
| JP | 2004290412 A | 10/2004 |
| JP | 2005533609 A | 11/2005 |
| JP | 2005535359 A | 11/2005 |
| JP | 2008532680 A | 8/2008 |
| JP | 2010534083 A | 11/2010 |
| WO | WO-0181798 A1 | 11/2001 |
| WO | WO-03063697 A1 | 8/2003 |
| WO | WO-2004010844 A2 | 2/2004 |
| WO | WO-2006094279 A1 | 9/2006 |
| WO | WO-2006124696 A1 | 11/2006 |
| WO | WO-2007012931 A2 | 2/2007 |
| WO | WO-2009013608 A2 | 1/2009 |
| WO | WO-2009013608 A3 | 1/2009 |
| WO | WO-2010056973 A1 | 5/2010 |

OTHER PUBLICATIONS

"U.S. Appl. No. 11/078,399, Final Office Action mailed Jun. 10, 2010", 12 pgs.

(56) References Cited

OTHER PUBLICATIONS

"U.S. Appl. No. 11/078,399, Non-Final Office Action mailed Dec. 3, 2009", 23 pgs.
"U.S. Appl. No. 11/078,399, Notice of Allowance mailed Sep. 1, 2010", 7 pgs.
"U.S. Appl. No. 11/078,399, Preliminary Amendment filed Jan. 7, 2009", 17 pgs.
"U.S. Appl. No. 11/078,399, Preliminary Amendment filed Mar. 10, 2006", 20 pgs.
"U.S. Appl. No. 11/078,399, Response filed Mar. 2, 2010 to Non Final Office Action mailed Dec. 3, 2009", 17 pgs.
"U.S. Appl. No. 11/078,399, Response filed Jul. 16, 2009 to Restriction Requirement mailed Jun. 16, 2009", 12 pgs.
"U.S. Appl. No. 11/078,399, Response filed Aug. 10, 2010 to Final Office Action mailed Jun. 10, 2010", 14 pgs.
"U.S. Appl. No. 11/078,399, Restriction Requirement mailed Jun. 16, 2009", 7 pgs.
"U.S. Appl. No. 11/780,997, Examiner Interview Summary mailed May 26, 2011", 4 pgs.
"U.S. Appl. No. 11/780,997, Final Office Action mailed Mar. 2, 2010", 10 pgs.
"U.S. Appl. No. 11/780,997, Final Office Action mailed Apr. 8, 2011", 15 pgs.
"U.S. Appl. No. 11/780,997, Non-Final Office Action mailed Jun. 5, 2009", 19 pgs.
"U.S. Appl. No. 11/780,997, Non-Final Office Action mailed Jun. 11, 2010", 12 pgs.
"U.S. Appl. No. 11/780,997, Notice of Allowance mailed Jul. 12, 2011", 7 pgs.
"U.S. Appl. No. 11/780,997, Response filed Apr. 29, 2010 to Final Office Action mailed Mar. 2, 2010", 12 pgs.
"U.S. Appl. No. 11/780,997, Response filed Jun. 8, 2011 to Final Office Action mailed Apr. 8, 2011", 15 pgs.
"U.S. Appl. No. 11/780,997, Response filed Oct. 5, 2009 to Non Final Office Action mailed Jun. 5, 2009", 25 pgs.
"U.S. Appl. No. 11/780,997, Response filed Oct. 12, 2010 to Non-Final Office Action mailed Jun. 11, 2010", 15 pgs.
"U.S. Appl. No. 12/618,120, Non Final Office Action mailed Jan. 7, 2013", 9 pgs.
"U.S. Appl. No. 12/618,120, Notice of Allowance mailed Sep. 3, 2013", 10 pgs.
"U.S. Appl. No. 12/618,120, Notice of Allowance mailed Dec. 24, 2013", 11 pgs.
"U.S. Appl. No. 12/618,120, Response filed Jul. 8, 2013 to Non Final Office Action mailed Jan. 7, 2013", 9 pgs.
"U.S. Appl. No. 12/618,120, Response filed Oct. 26, 2012 to Restriction Requirement mailed Jul. 26, 2012", 8 pgs.
"U.S. Appl. No. 12/618,120, Restriction Requirement mailed Jul. 26, 2012", 12 pgs.
"U.S. Appl. No. 12/946,506, Non Final Office Action mailed Jan. 7, 2013", 6 pgs.
"U.S. Appl. No. 12/946,506, Notice of Allowance mailed Mar. 14, 2014", 6 pgs.
"U.S. Appl. No. 12/946,506, Notice of Allowance mailed Aug. 20, 2013", 13 pgs.
"U.S. Appl. No. 12/946,506, Notice of Allowance mailed Dec. 6, 2013", 9 pgs.
"U.S. Appl. No. 12/946,506, Preliminary Amendment mailed Jun. 23, 2011", 8 pgs.
"U.S. Appl. No. 12/946,506, Response filed Jun. 7, 2013 to Non Final Office Action mailed Jan. 7, 2013", 19 pgs.
"U.S. Appl. No. 13/283,044, Preliminary Amendment filed Apr. 10, 2012", 6 pgs.
"European Application Serial No. 06795079.0, Amendment filed Feb. 12, 2014", 20 pgs.
"European Application Serial No. 06795079.0, Amendment filed Dec. 7, 2007", 28 pgs.
"European Application Serial No. 06795079.0, Office Action mailed Mar. 27, 2014", 25 pgs.
"European Application Serial No. 06795079.0, Office Action mailed Apr. 11, 2013", 5 pgs.
"European Application Serial No. 06795079.0, Office Action mailed Aug. 1, 2011", 6 pgs.
"European Application Serial No. 06795079.0, Office Action mailed Sep. 25, 2009", 5 pgs.
"European Application Serial No. 06795079.0, Office Action mailed Dec. 5, 2013", 5 pgs.
"European Application Serial No. 06795079.0, Response filed Mar. 25, 2010 to Office Action mailed Sep. 25, 2009", 12 pgs.
"European Application Serial No. 06795079.0, Response filed May 16, 2012 to Office Action mailed Mar. 20, 2012", 12 pgs.
"European Application Serial No. 06795079.0, Response filed Aug. 13, 2013 to Office Action mailed Apr. 11, 2013", 11 pgs.
"International Application Serial No. PCT/IB2006/001863, International Search Report mailed May 23, 2007", 5 pgs.
"International Application Serial No. PCT/IB2006/001863, Preliminary Report on Patentability mailed Sep. 18, 2007", 13 pgs.
"International Application Serial No. PCT/IB2006/001863, Written Opinion mailed Sep. 14, 2007", 12 pgs.
"International Application Serial No. PCT/IB2008/001932, International Preliminary Report on Patentability mailed Feb. 4, 2010", 8 pgs.
"International Application Serial No. PCT/IB2008/001932, International Search Report and Written Opinion dated Mar. 3, 2009", 13 pgs.
"International Application Serial No. PCT/US2009/064360, International Preliminary Report on Patentability mailed May 17, 2011", 7 pgs.
"International Application Serial No. PCT/US2009/064360, International Search Report mailed Mar. 9, 2010", 7 pgs.
"International Application Serial No. PCT/US2009/064360, Written Opinion mailed Mar. 9, 2010", 6 pgs.
"Japanese Application Serial No. 2008-501451, Amendment filed Mar. 9, 2009", w/English claims, 15 pgs.
"Japanese Application Serial No. 2008-501451, Office Action mailed Jan. 24, 2014", English translation, 9 pgs.
"Japanese Application Serial No. 2008-501451, Office Action mailed Feb. 8, 2013", w/English translation, 7 pgs.
"Japanese Application Serial No. 2008-501451, Office Action mailed Oct. 21, 2011", w/English translation, 8 pgs.
"Japanese Application Serial No. 2008-501451, Response filed Apr. 20, 2012 to Office Action mailed Oct. 21, 2011", w/English claims, 22 pgs.
"Japanese Application Serial No. 2008-501451, Response filed Jul. 8, 2013 to Office Action mailed Feb. 8, 2013", w/English translation, 14 pgs.
Graaff, R., "Reduced Light-Scattering Properties for Mixtures of Spherical Particles: A Simple Approximation Derived from Mie Calculations", Applied Optics 31, (1992), 1370-1376.
Keogh, Brian F., "When Pulse Oximetry Monitoring of the Critically Ill is Not Enough", Anesth Analg 94, (2002), S96-S99.
Page, Andrew J, et al., "Distributed Monte Carlo Simulation of Light Transportation in Tissue", (2006), 4 pgs.
Rais-Bahrami, K, et al., "Validation of a noninvasive neonatal optical cerebral oximeter in veno-venous ECMO patients with a cephalad catheter", Journal of Perinatology, (2006), 628-635.
Schmitt, Joseph M., "Simple Photon Diffusion Analysis of the Effects of Multiple Scattering on Pulse Oximetry", IEEE, vol. 38, No. 12, (Dec. 1991), 1194-1203.
U.S. Appl. No. 12/946,506, Notice of Allowance mailed Aug. 22, 2014, 7 pgs.
U.S. Appl. No. 13/283,044, Final Office Action mailed Jul. 10, 2015, 6 pgs.
U.S. Appl. No. 13/283,044, Non Final Office Action mailed Oct. 9, 2014, 8 pgs.
U.S. Appl. No. 13/283,044, Response filed Mar. 9, 2015 to Non Final Office Action mailed Oct. 9, 2014, 11 pgs.
Japanese Application Serial No. 2008-501451, Amendment and Argument filed on Jul. 24, 2014 in response to Office Action mailed Jan. 24, 2014, (w/ English Translation of Claims), 25 pgs.

(56) References Cited

OTHER PUBLICATIONS

Japanese Application Serial No. 2008-501451, Examiners Decision of Final Refusal mailed Sep. 9, 2014, (w/ English Translation), 6 pgs.
U.S. Appl. No. 13/283,044, Examiner Interview Summary mailed Sep. 10, 2015, 4 pgs.
U.S. Appl. No. 13/283,044, Examiner Interview Summary mailed Nov. 18, 2015, 3 pgs.
U.S. Appl. No. 13/283,044, Final Office Action mailed Aug. 11, 2015, 6 pgs.
U.S. Appl. No. 13/283,044, Notice of Allowance mailed Feb. 16, 2016, 5 pgs.
U.S. Appl. No. 13/283,044, Response filed Jan. 11, 2016 to Final Office Action mailed Aug. 11, 2015, 11 pgs.
U.S. Appl. No. 14/196,725, Preliminary Amendment filed May 22, 2014, 6 pgs.
U.S. Appl. No. 14/196,725, Response filed Mar. 15, 2016 to Restriction Requirement mailed Jan. 15, 2016, 11 pgs.
U.S. Appl. No. 14/196,725, Restriction Requirement mailed Jan. 15, 2016, 7 pgs.
U.S. Appl. No. 14/196,725, Supplemental Preliminary Amendment filed Jan. 14, 2015, 8 pgs.
Japanese Application Serial No. 2015-003173, Office Action mailed Jan. 28, 2016, 9 pgs.
Jacques, S.L., "Optical properties of biological tissues: a review", Phys. Med. Biol., 58, (2013), R37-R61.
U.S. Appl. No. 14/196,725, Non Final Office Action mailed Jun. 17, 2016, 6 pgs.

\* cited by examiner

OPTICAL SENSOR PATH SELECTION

CLAIM OF PRIORITY

This patent application is a divisional of and claims the benefit of priority, under 35 U.S.C. §120, to Isaacson, U.S. patent application Ser. No. 12/618,120, entitled "OPTICAL SENSOR PATH SELECTION," filed on Nov. 13, 2009, which claims the benefit of priority, under 35 U.S.C. §119 (e), to Isaacson, U.S. Provisional Patent Application Ser. No. 61/114,528, entitled "OPTICAL SENSOR PATH SELECTION," filed on Nov. 14, 2008, , and each of which are incorporated herein by reference in their entireties.

BACKGROUND

The human brain requires a continuous supply of oxygen. A measure of blood oxygenation can help to accurately diagnose a medical condition or monitor the health of a patient. Current technology for determining cerebral oximetry is inadequate.

SUMMARY

The present subject matter includes systems and methods as described herein. For example, a patient sensor includes a first emitter and a first detector separated by a first dimension and a second emitter and a second detector separated by a second dimension. The first dimension and the second dimension can be determined by a particular technique.

In one example, the sensor is fully compensated and include two emitters and two detectors. In this example, a first emitter and a first detector are coupled by a short path that traverses a surface layer of the tissue as well as an exclusion region within the tissue. The first emitter is also coupled to a second detector by a long path that traverses the surface layers of the tissue as well as a region of interest at a particular depth within the tissue. A second emitter is coupled to the first detector by a long path that traverses the surface layers of the tissue as well as the region of interest within the tissue. The second emitter is also coupled to the second detector by a short path that traverses the surface layers of the tissue and passes through exclusion region of the tissue without encroaching on the region of interest.

The mean depth of the light path is approximately one third of the distance between the emitter and the detector. According to one example, a method includes selecting a long path dimension and selecting a short path dimension for placement of detectors and emitters.

Consider first, selecting a long path dimension for a sensor having two emitters and two detectors. The long path dimension refers to the lateral separation between an emitter and a detector in which the path through the biological tissue traverses the region of interest. The long path dimension is proportional to the average depth of the region of interest. In one example, the region of interest is the cerebral cortex and the long path dimension is approximately 40 mm.

Next, consider selecting the short path dimension. The short path dimension also refers to the separation between an emitter and a detector. The short path dimension is selected to provide an optical path having a tissue depth that traverses a surface layer and does not traverse the region of interest. As with the long path dimension, the short path dimension is proportional to the penetration depth in the tissue. The optical path corresponding to the short path dimension is selected to be approximately three times the thickness of the surface layer to be excluded (e.g., the dermis and epidermis) and just short of the depth of the region of interest. A typical scalp thickness is approximately at least 3 mm and a typical skull thickness is approximately at least 5 mm which means that the minimum depth to the brain is approximately 8 mm. Thus, for cerebral oximetry the short path dimension is selected to be less than three times 8 mm (24 mm). In one example, the short path dimension is 20 mm.

More generally, the scalp depth is between approximately 3 mm and 10 mm and the skull depth is between approximately 5 mm and 10 mm.

For a neonate, typical dimensions are 3 mm for the scalp and 4 mm for the skull. As such, the long path dimension is at least approximately three times 7 mm (21 mm). In one example, the long path dimension is 25 mm. The short path dimension is at least three times the scalp thickness (9 mm) and less than 21 mm. In one example, the short path dimension is 12.5 mm.

In one example, the long path dimension is twice that of the short path dimension. For example, an adult cerebral oximetry sensor has a long path dimension and short path dimension of 25 mm and 12.5 mm, respectively and a neonate cerebral oximetry sensor has dimensions of 40 mm and 20 mm, respectively. The 2:1 ratio between long dimension and short dimension provides good compensation and good signal; however, other ratios are also contemplated.

This summary is intended to provide an overview of subject matter of the present patent application. It is not intended to provide an exclusive or exhaustive explanation of the invention. The detailed description is included to provide further information about the present subject matter.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present subject matter is directed to in vivo optical examination and monitoring of selected blood metabolites or constituents in human or other living subjects. Examination and monitoring can include transmitting selected wavelengths of light into a particular area of biological tissue and receiving the resulting light as it emerges from the area, and analyzing the received light to determine the desired data based on light absorption.

One example includes an optical sensor assembly that is particularly adapted for in vivo use as the patient interface in a patient-monitoring apparatus such as a cerebral or tissue oximeter.

One example can be used for non-invasive determination of tissue oxygenation or non-invasive cerebral oximetry. Cerebral oximetry provides a measure of blood oxygen saturation in the brain. One example includes an optical sensor having light emitters and detectors that can be applied to the forehead of the patient.

One example includes an apparatus for in vivo monitoring of blood metabolites such as hemoglobin oxygen concentration in any of a plurality of different regions of a patient through application of an optical sensor assembly. The optical sensor assembly is in communication with, or is coupled to, a processor. The processor can be configured to control the sensor and analyze data from the sensor. One example of a processor includes a monitor which provides a visible display based on the analysis.

The processor can be configured to operate the sensor. The sensor is configured to couple with tissue of the patient and emit and detect light energy. The sensor provides an output signal to the processor corresponding to the detected energy.

One example includes an optical probe configured to conform to a shape of the cerebrum or other anatomical area.

Figure 1:
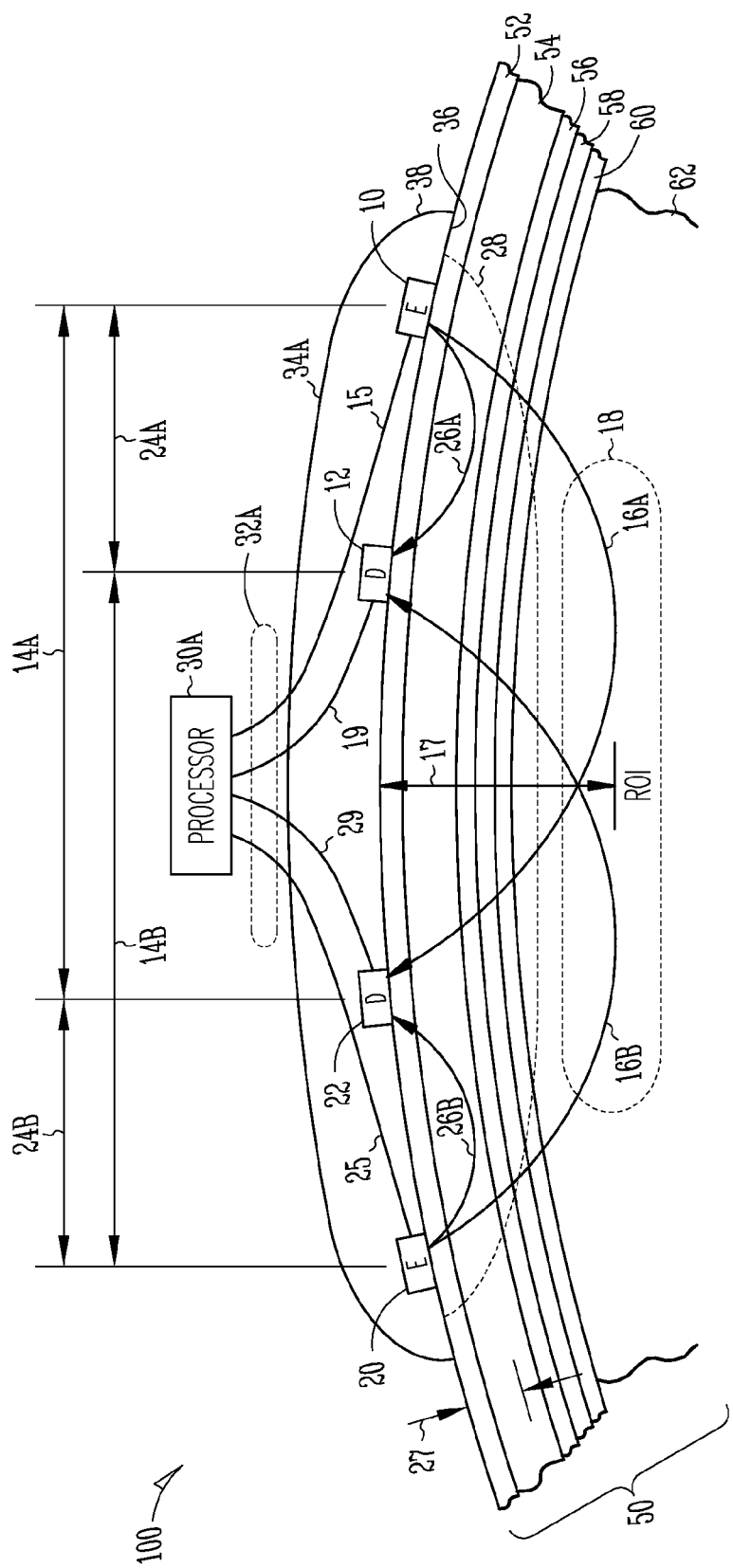
FIG. 1 includes a view of a sensor according to one example.

FIG. 1 illustrates view 100 including processor 30A, sensor 34A (in partial sectional view), and biological tissue 50 (also in partial sectional view) according to one example. Processor 30A is in communication with, or is coupled to, sensor 34A by link 32A. Processor 30A can include a digital processor, a central processor unit (CPU), a microprocessor, a computer, a digital signal processor, an application specific integrated circuit (ASIC), an analog processor, or a mixed signal processor. In addition, processor 30A can include a memory or other device for storing instructions or data. Processor 30A can include other elements as well, including, for example, an analog-to-digital converter (ADC), a digital-to-analog converter (DAC), a driver, an amplifier, a filter, or other circuitry to perform a method as described herein.

Link 32A can include a wired or wireless channel. Link 32A can convey an instruction or control signal. Link 32A can convey a communication signal or data corresponding to a detected signal.

Sensor 34A includes housing 38 having a surface 36. Housing 38 can be rigid or flexible and is configured for coupling to biological tissue 50 at surface 36. In the example shown, surface 36 is closely conformed to the contours of biological tissue 50. Sensor 34A can be affixed to biological tissue by adhesive, a strap, a band, a clamp, or other means.

Sensor 34A includes first emitter 10, second emitter 20, first detector 12, and second detector 22. Emitters 10 and 20 and detectors 12 and 22 are positioned about surface 36 in a manner that allows optical signals to freely pass between sensor 34A and biological tissue 50. In one example, emitters 10 and 20 and detectors 12 and 22 are mounted to an electrical circuit (such as a printed wire board, a substrate, rigid circuit board, or flexible circuit material) within sensor 34A and optical energy passes through an aperture or window in surface 36.

In one example, at least one of first emitter 10 and second emitter 20 includes a light emitting diode (LED). In the figure, first emitter 10 and second emitter 20 are shown as unitary devices but in various examples, either can include multiple individual LEDs configured to produce light of a particular wavelength. In one example, first emitter 10 and second emitter 20 include a fiber-optic element. The energy emitted by emitter 10 or emitter 20 can include visible light, infrared energy, and near infrared energy. In one example, first emitter 10 produces light of a particular wavelength and second emitter 20 produces light of a different wavelength. First emitter 10 and second emitter 20 are coupled to processor 30A by link 15 and link 25, respectively.

In one example, at least one of first detector 12 and second detector 22 includes a photodetector. First detector 12 and second detector 22 are configured to generate an output based on received energy having a particular wavelength. The sensitivities of first detector 12 and second detector 22 can be selected (or adjusted) to generate an output for particular wavelengths. First detector 12 and second detector 22 are coupled to processor 30A by link 19 and link 29, respectively.

In addition to sensor 34A, FIG. 1 illustrates biological tissue 50. Biological tissue 50, in the example shown, depicts a portion of a human forehead; however other biological tissue can be monitored as well. For example, the present subject matter can be used with an arm, a finger (or thumb), a toe, an ear lobe, and a torso.

Biological tissue 50, as illustrated, includes a plurality of layers. As shown in the figure, the layers include scalp 52, skull 54, dura 56, arachnoid 58, pia mater 60, and cerebral cortex 62. In the figure, each layer has a relatively uniform thickness however; this can vary from site to site of a particular patient as well as from one patient to the next. A typical thickness for scalp 52 is in the range of 3 mm to 10 mm and for skull 54, the typical thickness is between 5 mm and 10 mm. As such, the brain (cerebral cortex) is typically at a depth of greater than 8 mm below the exterior surface of scalp 52.

FIG. 1 illustrates region of interest 18 and exclusion region 28. In the example shown, region of interest 18 lies wholly within the layer of cerebral cortex 62 at an average depth denoted by first depth 17. Region of interest 18 is representative of a portion of the cerebral cortex. Exclusion region 28 extends from the surface of biological tissue 50 to nearly the region of interest 18 and has an average depth denoted by second depth 27. Exclusion region 28, in the example shown includes scalp 52, skull 54, dura 56, arachnoid 58, pia mater 60, and a portion of cerebral cortex 62.

In other examples, region of interest 18 and exclusion region 28 may occur in layers other than that shown in the figure. For example, region of interest 18 can lie in cerebral cortex 62 and exclusion region 28 can include the layers of dura 56, arachnoid 58, and pia mater 60. In one example, region of interest 18 can lie in a first portion of cerebral cortex 62 and exclusion region 28 can include a second portion of cerebral cortex 62 where the first portion has a depth of 10 mm and the second portion has a depth of 8 mm. The depth of exclusion region 28 is less than the depth of the region of interest 18.

As shown in the figure, energy emitted from first emitter 10 can be modeled by path 16A and by path 26A. Path 16A enters biological tissue 50, traverses region of interest 18, and emerges from biological tissue 50 and the resulting energy is detected by second detector 22. Path 26A enters biological tissue 50, traverses exclusion region 28, and emerges from biological tissue 50 and the resulting energy is detected by first detector 12. In a similar manner, energy emitted from second emitter 20 can be modeled by path 16B and by path 26B. Path 16B enters biological tissue 50, traverses region of interest 18, and emerges from biological tissue 50 and the resulting energy is detected by first detector 12. Path 26B enters biological tissue 50, traverses exclusion region 28, and emerges from biological tissue 50 and the resulting energy is detected by second detector 22.

To the extent that paths 16A and 16B and paths 26A and 26B are models, the actual path followed by energy delivered by sensor 34A may be different than that shown. For example, light scattering and other optical effects can change the actual path through biological tissue 50. Paths 16A, 16B, 26A, and 26B represent a mean path by which light traverses biological tissue 50. In general, the light traverses the tissue in a curved shape that resembles a banana.

Path 16B and path 26A illustrate that energy detected by first detector 12 originates from second emitter 20 and first emitter 10, respectively. In a similar manner, path 26B and path 16A illustrate that energy detected by second detector 22 originates from second emitter 20 and first emitter 10, respectively.

First emitter 10 is separated from first detector 12 by a lateral distance denoted in the figure as dimension 24A and is separated from second detector 22 by a lateral distance denoted in the figure as dimension 14A. In a similar manner, second emitter 20 is separated from second detector 22 by a lateral distance denoted in the figure as dimension 24B and is separated from first detector 12 by a lateral distance denoted in the figure as dimension 14B. Dimension 14A and dimension 14B are approximately equal and dimension 24A and dimension 24B are approximately equal. Dimension 14A (and thus dimension 14B) is approximately twice the length of dimension 24A (and thus dimension 24B), thus having a ratio of approximately 2:1.

The depth of energy penetration into biological tissue 50, and thus the depth of the region (region of interest 18 or exclusion region 28) are proportional to the corresponding lateral distance. To a close approximation, the depth of penetration is approximately one third the lateral distance at the surface of biological tissue 50.

Figure 2:
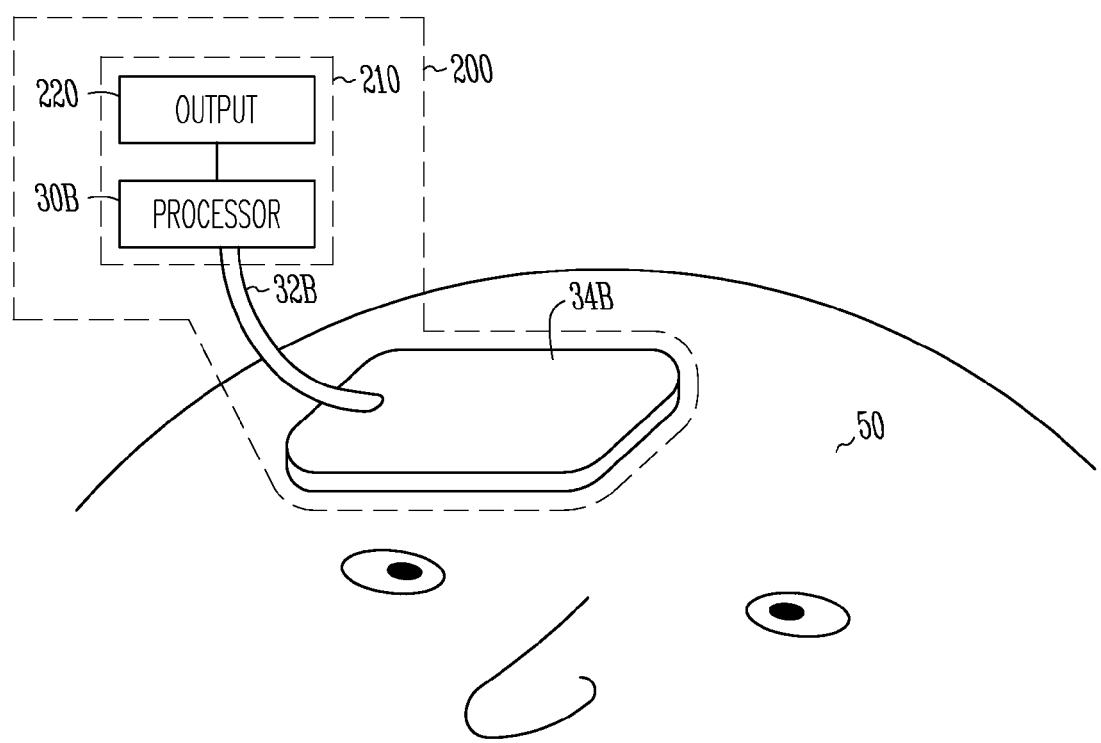
FIG. 2 includes a system according to one example.

FIG. 2 illustrates system 200 according to one example. System 200 includes sensor 34B coupled by link 32B to a module, here shown to include processor 30B. Sensor 34B is affixed to a forehead of biological tissue 50 (depicted herein as that of an infant or neonate), however, sensor 34B can be affixed to another particular site of a human. Sensor 34B includes a pair of emitters and a pair of detectors as described elsewhere in this document, and in the example shown, is depicted as adhesively coupled to tissue 50. Link 32B is illustrated as a wired connection however, a wireless coupling is also contemplated. For example, link 32B can include an optical fiber or a short-range radio frequency (RF) transceiver.

Processor 30B is shown coupled to output 220. Output 220 can include, in various examples, a visual display, a memory, a printer, a network (data or communication), a speaker, or other such device. In one example, processor 30B generates a processor output that is communicated to output 220. In one example, processor 30B and output 220 are part of a stand-alone unit typically referred to as monitor 210. Monitor 210 can be configured for patient use or for use by medical personnel.

Figure 3:
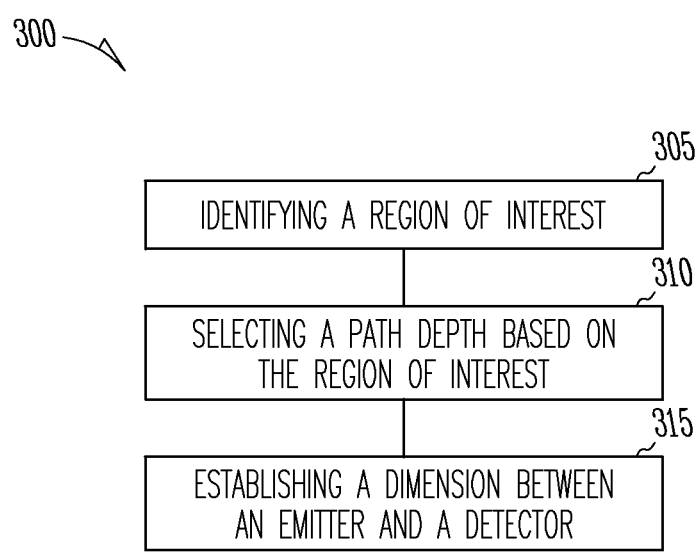
FIG. 3 includes a method according to one example.

FIG. 3 includes method 300 according to one example. At 305, method 300 includes identifying a region of interest. The region of interest can include the cerebral cortex, a muscle, or other substance at a particular depth within biological tissue. At 310, method 300 includes selecting a path depth based on the region of interest. The path traverses the biological tissue and the region of interest at a particular depth. In the example shown in FIG. 1, a representative path depth is depicted as first depth 17.

The path can be projected onto an adjacent surface of the biological tissue to yield a spacing dimension. At 315, method 300 includes establishing the dimension between the emitter and the detector. As shown in the example of FIG. 1, this corresponds to, for example, dimension 14A. For some biological tissue, the path length and depth are related by ratio of 3:1.

Method 300 represents a general procedure for selection of a path length. The discussion has focused on the region of interest but a similar calculation can be performed for the region denoted earlier as the exclusion region.

Figure 4:
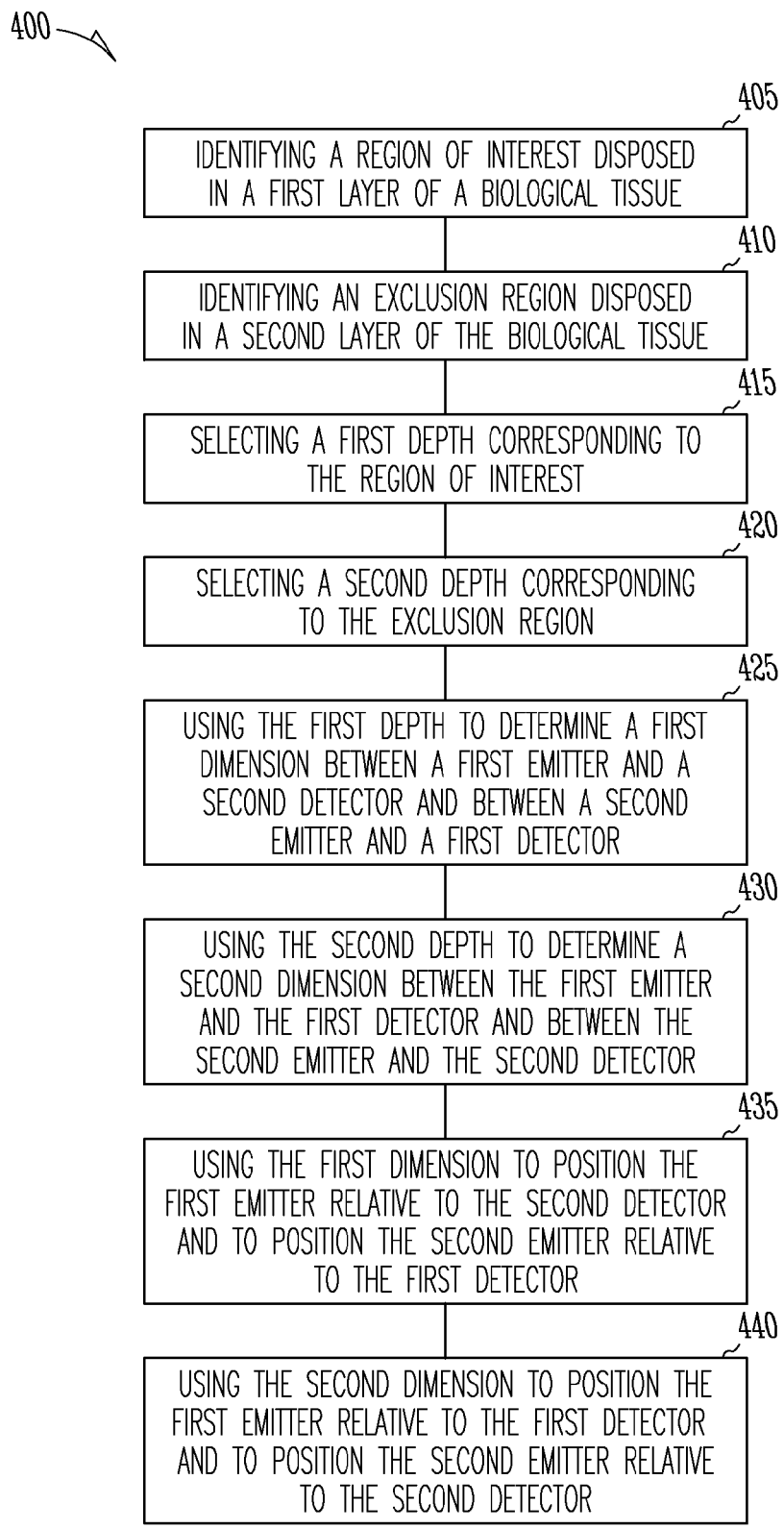
FIG. 4 includes a method according to one example.

FIG. 4 includes method 400 according to one example. At 405, method 400 includes identifying a region of interest disposed in a first layer of a biological tissue. With respect to the example of FIG. 1, region of interest 18 lies in the layer of cerebral cortex 62 of biological tissue 50. At 410, method 400 includes identifying an exclusion region disposed in a second layer of the biological tissue.

FIG. 1 illustrates exclusion region 28 within the layer of scalp 52, skull 54, dura 56, arachnoid 58, pia mater 60, and also cerebral cortex 62. As shown, exclusive region 28 occupies a different layer than that of region of interest 18. In particular, the regions are exclusive of each other. In addition, the depth of region of interest 18 (depth 17) is greater than that of the depth of exclusion region 28 (depth 27).

At 415, method 400 includes selecting a value for depth 17 corresponding to region of interest 18, and at 420, selecting a value for depth 27 corresponding to the exclusion region 28. The second depth is less than the first depth, and in one example, the second depth is less than 80 percent of the first depth. For example, with an 8 mm value for first depth 17, the value for second depth 27 is 6.4 mm.

At 425, method 400 includes using depth 17 to determine dimension 14A (between first emitter 10 and second detector 22) and to determine dimension 14B (between second emitter 20 and first detector 12).

At 430, method 400 includes using depth 27 to determine dimension 24A (between first emitter 10 and first detector 12) and to determine dimension 24B (between second emitter 20 and second detector 22).

With reference to FIG. 1, first detector 12 generates a first output based on the optical coupling with first emitter 10 (via exclusion region 28) and second emitter 20 (via region of interest 18). The first output from first detector 12 can include an analog or digital signal provided by a photodetector. In similar manner, second detector 22 generates a second output based on the optical coupling with second emitter 20 (via exclusion region 28) and first emitter 10 (via region of interest 18).

Processor 30A uses the first output (from first detector 12) and the second output (from detector 22) to determine a parameter for the biological tissue. The parameter, for example can include a measure of blood oximetry or tissue oximetry.

The first output and the second output can be configured to selectively correspond to the region of interest 18 or the exclusion region 28. For example, an emitter (such as emitter 10 or emitter 20) can be configured to produce a particular wavelength of light. In addition, a detector (such as detector 12 or detector 22) can be configured for sensitivity to light having a particular wavelength.

In one example, the emitters and the detectors are sequentially activated. For example, the emitters are sequentially powered and then un-powered in order to generate data corresponding to the different path lengths. Other techniques and arrangements to encode the data produced by the various emitter-detector pairs are also contemplated.

With reference to both FIG. 4 and FIG. 1, at 435, method 400 includes using a calculated dimension 14A to position first emitter 10 relative to second detector 22 in housing 38 of sensor 34A and using approximately the same dimension 14B to position second emitter 20 relative to first detector 12. In one example, this includes affixing first emitter 10 and first detector 12 at a spacing of 40 mm.

At 440, method 400 includes using a calculated dimension 24A to position first emitter 10 relative to first detector 12 in housing 38 and using approximately the same dimension 24B to position second emitter 20 relative to second detector 22 in housing 38. In one example, this includes affixing second emitter 20 and second detector 22 at a spacing of 20 mm. Sensor 34A is configured to determine a physiological parameter of biological tissue 50.

In one example, processor 30A executes instructions to determine oxygenation or other physiological parameter using the first output (from first detector 10) and the second output (from second detector 20). This can include executing an instruction to perform an algorithm wherein the instructions are stored in a memory accessible to processor 30A. In one example, the instructions can include using a look-up table stored in a memory.

In one example, first dimension 14A (and dimension 14B) and second dimension 24A (and dimension 24B) are related by a ratio of 2:1. In other words, the value of dimension 14A is twice that of dimension 24A. For example, first dimension 14A and second dimension 24A can be 40 mm and 20 mm, respectively, or 25 mm and 12.5 mm, respectively.

Additional Examples

The arrangement of optical elements (emitters and detectors) in FIG. 1 can be modeled as emitter-detector-detector-emitter and the dimensions between the various elements can be determined as described elsewhere in this document. For a sensor having four elements a variety of arrangements having a different layout, different spacing, or a different order of elements are contemplated. For example, the elements can be arranged as detector-emitter-emitter-detector, as detector-detector-emitter-emitter, or as detector-emitter-detector-emitter.

A sensor can have three elements including, for example, two detectors and a single emitter. As with the other configurations described herein, the short dimension is selected to produce a shallow path through an exclusion region of the tissue and the long dimension is selected to produce a deep path through a region of interest in the tissue.

In addition, a sensor having more than four elements is also contemplated. The elements can be arranged in an array of emitters and a corresponding array of detectors. Either or both array can be of a single dimension (e.g., an array of four emitters) or of two dimensions (e.g., an array of three detectors by four detectors).

In one example, a first housing of the sensor can include one or more emitters and a second housing of the sensor can include one or more detectors. The first housing and the second housing are coupled by a wired or wireless link and the placement of the housings is user selectable.

In one example, a sensor includes a number of detectors that differs from a number of emitters. For example, a particular sensor can have a single emitter and two detectors wherein the path through the region of interest differs from the path through an exclusion region, and thus, the first dimension differs from second dimension as described elsewhere in this document. In one example, more than two emitters and more than two detectors are included in a particular sensor.

In one example, a sensor includes an array of emitters in which the array is configured with individual elements that can selectively emit energy in order to provide a variable dimension. In a similar manner, one example includes an array of photodetector elements, also configured for individual selection to provide a variable dimension.

In one example, an emitter produces a white light and a particular detector is configured for sensitivity for a particular wavelength of light corresponding to the parameter being measured.

In one example processor 30A calculates a physiological parameter using an algorithm in which the optical absorbance corresponding to the short paths is subtracted from the optical absorbance corresponding to the long paths.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A device comprising:
   a housing having a surface for coupling to a biological tissue;
   an array of emitters, the array including at least a first emitter and a second emitter, the array coupled to the surface;
   a first detector and a second detector coupled to the surface, the first detector having a first output and the second detector having a second output;
   the array coupled to a processor and wherein the processor is configured to select the first emitter and the second emitter from the array of emitters, wherein the first emitter and the second detector are separated by a first dimension and the second emitter and the first detector are separated by approximately the first dimension, the first dimension selected to correspond with a region of interest in a first layer of the biological tissue, the first emitter and the first detector are separated by a second dimension and the second emitter and the second detector are separated by approximately the second dimension, the second dimension selected to correspond with an exclusion region in a second layer of the biological tissue, the first layer having a first depth below the surface and the second layer having a second depth below the surface, the first depth greater than the second depth, and wherein the first emitter and the second emitter are configured to be sequentially powered and unpowered, and wherein the first dimension and the second dimension correspond to the selected emitters; and
   a port coupled to the housing and configured to communicate at least one of the first output or the second output to a module.

2. The device of claim 1 wherein the first dimension is approximately 40 mm.

3. The device of claim 1 wherein the first dimension is approximately 25 mm.

4. The device of claim 1 wherein the housing is configured for adhering to a forehead.

5. The device of claim 1 wherein at least one of the first emitter and the second emitter includes a light emitting diode (LED).

6. A system comprising:
   a sensor configured to couple with a biological tissue, the sensor having an array of emitters, the array including at least a first emitter and a second emitter, the sensor having a first detector and a second detector the first detector having a first output and the second detector having a second output; and
   a processor coupled to the sensor and configured to generate a processor output using the first output and the second output, the processor output corresponding to a physiological parameter of the biological tissue, and wherein the processor is configured to sequentially power and unpower the first emitter and the second emitter, and wherein the processor is configured to select the first emitter and the second emitter from the array of emitters, wherein the first emitter and the second detector are separated by a first dimension and the second emitter and the first detector are separated by approximately the first dimension, the first dimension selected to correspond with a region of interest in a first layer of the biological tissue, the first emitter and the first detector are separated by a second dimension and the second emitter and the second detector are separated by approximately the second dimension, the second dimension selected to correspond with an exclusion region in a second layer of the biological tissue, the first layer having a first depth below the surface and the second layer having a second depth below the surface, the first depth greater than the second depth and wherein the first dimension and the second dimension correspond to the selected emitters.

7. The system of claim 6 wherein the first dimension is approximately 40 mm.

8. The system of claim 6 wherein the first dimension is approximately 25 mm.

9. The system of claim 6 wherein the sensor includes a surface configured to couple with the biological tissue, the first emitter and the second emitter configured to emit light through the surface and the first detector and the second detector configured to receive light through the surface.

10. The system of claim 6 wherein the processor is coupled to the sensor by at least one of a wired or wireless link.

11. The system of claim 6 wherein the processor output corresponds to oximetry of the biological tissue.

* * * * *